(12) United States Patent
Maciejewski et al.

(10) Patent No.: US 10,571,534 B2
(45) Date of Patent: Feb. 25, 2020

(54) MEDICAL IMAGING APPARATUS WITH A HOUSING

(71) Applicant: Siemens Healthcare GmbH, Erlangen (DE)

(72) Inventors: Bernd Maciejewski, Markt Erlbach (DE); Stephan Zink, Erlangen (DE); Mauro Mameli, Amberg (DE)

(73) Assignee: Siemens Healthcare GmbH, Erlangen (DE)

( * ) Notice: Subject to any disclaimer, the term of this patent is extended or adjusted under 35 U.S.C. 154(b) by 183 days.

(21) Appl. No.: 15/720,021

(22) Filed: Sep. 29, 2017

(65) Prior Publication Data
US 2018/0095148 A1    Apr. 5, 2018

(30) Foreign Application Priority Data
Sep. 30, 2016    (DE) .................... 10 2016 219 077

(51) Int. Cl.
| | | |
|---|---|---|
| *A61B 5/055* | (2006.01) | |
| *G01R 33/34* | (2006.01) | |
| *G01R 33/38* | (2006.01) | |
| *G01R 33/385* | (2006.01) | |
| *A61B 5/00* | (2006.01) | |

(52) U.S. Cl.
CPC ........ *G01R 33/34007* (2013.01); *A61B 5/055* (2013.01); *A61B 5/704* (2013.01); *G01R 33/3403* (2013.01); *G01R 33/3802* (2013.01); *G01R 33/3854* (2013.01); *A61B 2560/0406* (2013.01)

(58) Field of Classification Search
CPC .......... G01R 33/34007; G01R 33/3854; G01R 33/3403; A61B 5/055
USPC ........................................................ 324/322
See application file for complete search history.

(56) References Cited

U.S. PATENT DOCUMENTS

| | | | | |
|---|---|---|---|---|
| 4,774,486 | A * | 9/1988 | Moritsu ............ | G01R 33/3854 324/318 |
| 5,084,676 | A * | 1/1992 | Saho .................. | G01R 33/3854 324/318 |
| 5,235,283 | A * | 8/1993 | Lehne ................ | G01R 33/3854 324/318 |
| 5,577,504 | A * | 11/1996 | Salloway ............ | G01R 33/283 324/318 |
| 5,630,415 | A * | 5/1997 | Kaufman ............ | G01R 33/385 324/318 |
| 6,414,489 | B1 * | 7/2002 | Dean .................. | G01R 33/3854 324/318 |
| 6,564,900 | B1 * | 5/2003 | Dean .................. | G01R 33/3854 181/202 |
| 2001/0022515 | A1 * | 9/2001 | Yamashita ......... | G01R 33/3854 324/300 |
| 2003/0016018 | A1 * | 1/2003 | Arz .................... | G01R 33/3854 324/322 |
| 2003/0080742 | A1 * | 5/2003 | Stofiel ................ | F16F 15/02 324/322 |

(Continued)

*Primary Examiner* — Patrick Assouad
*Assistant Examiner* — Demetrius R Pretlow
(74) *Attorney, Agent, or Firm* — Schiff Hardin LLP (57) ABSTRACT

A medical imaging apparatus has medical image data detector, and a housing that at least partially surrounds the detector and has at least one cladding. The at least one cladding is a self-supporting cladding with a reinforcing grid and a resilient cladding layer.

21 Claims, 5 Drawing Sheets

(56) References Cited

U.S. PATENT DOCUMENTS

| | | | | |
|---|---|---|---|---|
| 2004/0021467 A1* | 2/2004 | Eberler | G01R 33/34007 | 324/318 |
| 2004/0178792 A1* | 9/2004 | Edelstein | G01R 33/3854 | 324/318 |
| 2005/0134269 A1* | 6/2005 | Feenan | G01R 33/3854 | 324/318 |
| 2006/0273793 A1* | 12/2006 | Roozen | G01R 33/3854 | 324/318 |
| 2009/0044212 A1* | 2/2009 | Dietz | A61B 6/10 | 720/651 |
| 2009/0260917 A1* | 10/2009 | Maciejewski | F16F 15/02 | 181/207 |
| 2010/0109668 A1* | 5/2010 | Maciejewski | G01R 33/3802 | 324/318 |
| 2011/0025329 A1* | 2/2011 | Utturkar | G01R 33/3403 | 324/318 |
| 2011/0291656 A1* | 12/2011 | Maciejewski | G01R 33/3854 | 324/318 |
| 2012/0293173 A1* | 11/2012 | de Lima | G01R 33/34007 | 324/318 |
| 2013/0002252 A1* | 1/2013 | Kidane | G01R 33/3854 | 324/322 |
| 2013/0043870 A1* | 2/2013 | de Lima | G01R 33/34007 | 324/318 |
| 2013/0048415 A1* | 2/2013 | de Lima | G10K 11/168 | 181/256 |
| 2013/0066187 A1* | 3/2013 | Maciejewski | G01R 33/3802 | 600/407 |
| 2013/0162254 A1* | 6/2013 | Hierl | G01R 33/3854 | 324/319 |
| 2013/0200896 A1 | 8/2013 | Maciejewski | | |
| 2013/0234709 A1* | 9/2013 | Hierl | G01R 33/28 | 324/318 |
| 2013/0234713 A1* | 9/2013 | Maciejewski | G01R 33/34007 | 324/321 |
| 2013/0237805 A1* | 9/2013 | Dietz | G01R 33/3854 | 600/410 |
| 2014/0008143 A1* | 1/2014 | Eberler | F16F 7/00 | 181/202 |
| 2014/0021949 A1* | 1/2014 | Heismann | G01R 33/34 | 324/307 |
| 2014/0125341 A1* | 5/2014 | Kwak | G01R 33/3854 | 324/322 |
| 2014/0225616 A1* | 8/2014 | Maciejewski | G01R 33/34 | 324/318 |
| 2015/0048827 A1* | 2/2015 | Watanabe | G01R 33/3858 | 324/318 |
| 2015/0061677 A1* | 3/2015 | Tsujita | G01R 33/3858 | 324/318 |
| 2016/0216349 A1 | 7/2016 | Takamori | G01R 33/3854 | |
| 2018/0059196 A1* | 3/2018 | Takamori | G01R 33/385 | |

* cited by examiner

MEDICAL IMAGING APPARATUS WITH A HOUSING

BACKGROUND OF THE INVENTION

Field of the Invention

The present invention concerns a medical imaging apparatus with a medical image data detector and a housing that at least partially surrounds the detector, and that has a cladding.

Description of the Prior Art

Very high operating sound levels may be generated during a medical imaging examination, in particular a magnetic resonance examination. For example, in magnetic resonance examinations very high operating sound levels and/or noise may be caused by the interaction between gradient coils and the basic field magnet of a magnetic resonance scanner. Patients find these high sound levels during the medical imaging examination troublesome.

SUMMARY OF THE INVENTION

An object of the present invention is to minimize sound transmission into the patient accommodation zone of a medical data detector during a medical imaging examination, in particular a magnetic resonance examination.

The invention is based on a medical imaging apparatus, in particular a magnetic resonance apparatus, which has a medical image data detector and a housing that at least partially surrounds the detector, and that has a cladding.

The cladding in accordance with the invention is a self-supporting cladding, which has a reinforcing grid and a resilient cladding layer. In this context, a self-supporting cladding means a cladding having a shape and stability so that the cladding does not need any additional strengthening or support in order to stay in place with a given shape on the detector. These properties are given to the cladding by the reinforcing grid of the self-supporting cladding. The self-supporting cladding has a rigidity, in particular a dimensional stability, arising solely from the grid. The shape and/or stability of the self-supporting cladding is accordingly achieved and/or obtained without additional supporting elements of the housing. The self-supporting cladding, in particular the reinforcing grid together with the resilient cladding layer, is preferably formed in one piece.

The reinforcing grid of the self-supporting cladding preferably is a dimensionally stable reinforcing grid that is arranged within the self-supporting cladding. It is the reinforcing grid which imparts the self-supporting function to the cladding. The reinforcing grid preferably is a rigid foam core with a Shore D hardness of 65±5.

The resilient cladding layer preferably has the characteristic of changing its shape on the application of a force thereto and, on removal of the applied force, of returning to the original shape that the resilient cladding layer had prior to application of force. The resilient cladding layer preferably is composed of a resilient foam material.

The reinforcing grid preferably performs the self-supporting function within the self-supporting cladding. The resilient cladding layer performs a cladding function of the self-supporting cladding.

As a result, it is advantageously possible to provide a particularly resilient cladding with elevated noise control by forming the self-supporting cladding with the resilient cladding composed of a foam material. In addition, simple installation of the self-supporting cladding is enabled. Moreover, the self-supporting cladding responds sluggishly to acoustic excitation and/or vibrations. Furthermore, despite the resilience of the cladding, forming the self-supporting cladding with the resilient cladding means that it is advantageously possible to dispense with additional noise control elements, such as additional foam moldings for muffling noise in transitional zones between two components.

The self-supporting cladding may be used in any medical imaging apparatus as appear appropriate to those skilled in the art. The self-supporting cladding is particularly suitable in a magnetic resonance apparatus, since in this case, due to the high operating sound levels of the magnetic resonance scanner, cladding according to the invention is particularly useful for noise reduction in the patient accommodation zone. The self-supporting cladding here preferably forms an inlet funnel of a magnetic resonance scanner housing, which covers the gradient coil arrangement.

In an embodiment of the invention, the reinforcing grid is at least partially embedded within the resilient cladding layer. As used herein, embedded means that at least individual subzones of the reinforcing grid, such as grid rods of the reinforcing grid, are surrounded, in particular directly surrounded, on at least two sides by the resilient cladding layer. At least individual subzones of the reinforcing grid, such as grid rods of the reinforcing grid, are preferably surrounded, in particular directly surrounded, on at least three sides by the resilient cladding layer. At least individual subzones of the reinforcing grid, such as grid rods of the reinforcing grid, are preferably surrounded, in particular directly surrounded, on all sides by the resilient cladding layer. Virtually all the subzones of the reinforcing grid are advantageously embedded within the resilient cladding layer.

This configuration of the self-supporting cladding permits a particularly compact structure of the self-supporting cladding, in which a particularly small thickness, namely a material thickness, of the self-supporting cladding can be provided. The self-supporting cladding may have a thickness, in particular a material thickness, of approx. 20 mm. The consequent compactness of the self-supporting cladding additionally permits simple installation of the self-supporting cladding.

The reinforcing grid may be a uniform reinforcing grid. A uniform reinforcing grid means that subzones between two adjacent grid rods in at least one direction, such as in a circumferential direction of the reinforcing grid, have an identical size, in particular an identical length. The respective spacings between each two grid rods in the circumferential direction of the reinforcing grid are preferably equal in size. This permits stability and/or dimensional stability of the self-supporting cladding.

The reinforcing grid may have two or more grid rods that are concentric to one another. Grid rods that are concentric to one another means two or more grid rods of annular construction, the radii of which are oriented about a common center point. In this manner, a load on defined zones of the reinforcing grid, in particular curved zones of the reinforcing grid, may be advantageously distributed, resulting in high stability and/or dimensional stability of the self-supporting cladding.

In an embodiment, the reinforcing grid has two or more grid rods that enclose a grid interspace in a planar manner, and the two or more grid rods are arranged trapezoidally around the grid interspace. This permits a uniform arrangement of the individual grid rods relative to one another, wherein adjacent grid rods are in each case identically spaced from one another in at least one direction, namely in a circumferential direction. In this manner, a load on defined zones of the reinforcing grid, in particular curved zones of the reinforcing grid, may furthermore likewise be advantageously distributed, resulting in high stability and/or dimensional stability of the self-supporting cladding.

In a further embodiment of the invention, the two or more grid rods have a spacing of at least 1 cm. The two or more grid rods may alternatively have a spacing of at least 2 cm or at least 3 cm. The two or more grid rods may have a spacing of at most 30 cm. The two or more grid rods may alternatively have a spacing of at most 25 cm or a spacing of at most 20 cm or a spacing of at most 15 cm. The two or more grid rods most preferably have a spacing of at least 4 cm and at most 6 cm. As a result, it is possible to achieve an advantageous resilience of the self-supporting cladding simultaneously combined with high stability and high dimensional stability of the self-supporting cladding within the housing.

In a further embodiment the reinforcing grid is a material that has a Shore D hardness of at least 50 and at most 70. The reinforcing grid may alternatively be a material with a Shore D hardness of at least 53 and at most 69 or a material with a Shore D hardness of at least 56 and at most 68 or a material with a Shore D hardness of at least 59 and at most 67 or a material with a Shore D hardness of at least 62 and at most 66 or a material with a Shore D hardness of 65. The material of the reinforcing grid is preferably an elastomer, in particular a tough elastomer, such as a rigid foam or a structural foam.

This embodiment of the invention has the advantage that the reinforcing grid has high rigidity and dimensional stability and simultaneously assists the resilience of the resilient cladding layer. The reinforcing grid can be constructed with a wall thickness of approx. 12 mm, thus providing a particularly stable and compact self-supporting cladding.

In another embodiment of the invention, the resilient cladding layer is a material that has a Shore A hardness of at least 50 and at most 70 or a material with a Shore A hardness of at least 52 and at most 68 or a material with a Shore A hardness of at least 54 and at most 66 or a material with a Shore A hardness of at least 56 and at most 64 or a material with a Shore A hardness of at least 58 and at most 62 or a material with a Shore A hardness of 60. The material of the resilient cladding layer preferably is an elastomer, in particular a flexible elastomer, such as a flexible foam or a structural foam.

This embodiment of the invention has the advantage that the resilient cladding layer has high resilience and additionally assists a high rigidity and dimensional stability of the reinforcing grid. A resilient cladding layer configured in this manner is also capable of achieving a high level of attenuation or muffling of sound waves in the event of sound wave propagation, such that propagation of high operating sound levels may advantageously be reduced, in particular in magnetic resonance apparatuses. This may have a soothing effect on the patient under examination, who therefore moves less during the medical imaging examination, in particular the magnetic resonance examination. This improves the image quality of the acquired medical image data.

As used herein, structural foam means a foam having a density that continuously inwardly decreases from the outside. Such a structural foam preferably has a porous core and a virtually solid peripheral zone. A structural foam is typically produced by injecting a mixture of, for example, polyol and isocyanate into a mold in which the mixture foams. Structural foams primarily include polyurethane, polystyrene, polyol, polyester and/or polyisocyanate materials.

In a further embodiment, the reinforcing grid has grid interspaces and the grid interspaces are at least partially filled with the resilient cladding layer. This provides an advantageous noise control barrier with regard to propagation of sound waves, in particular the high operating sound levels of a magnetic resonance apparatus. Preferably, all the grid interspaces are filled with the resilient cladding layer, such that it is possible to provide a continuous noise control barrier against propagation of sound waves, in particular the high operating sound levels of a magnetic resonance apparatus. Such a planar noise control barrier permits effective attenuation of sound waves.

The at least one self-supporting cladding may have a side that is remote from the image data detector (scanner), and the resilient cladding layer may form a surface of the side remote from the detector. A particularly smooth and uniform surface or surface structure thus is achieved on the side of the housing that faces the user. This provides a planar noise control barrier that is not interrupted by the reinforcing grid, thereby achieving effective attenuation and reduction of sound waves within the self-supporting cladding.

In a further embodiment, the housing has at least one further cladding and the at least one self-supporting cladding has at least one sealing element arranged on a peripheral zone, which adjoins the further cladding, of the at least one self-supporting cladding. Sealing of the housing is thereby achieved without additional, in particular separate, sealing components. With the at least one sealing element, the housing is at least partially sealed with regard to propagation of sound waves as well as with regard to undesirable penetration of liquids into the medical imaging apparatus. In this peripheral zone, thus in the region of the at least one sealing element, the self-supporting cladding may have a thickness of approx. 4 mm.

In a further embodiment of the invention, the resilient cladding layer includes the at least one sealing element. The resilient cladding layer is constructed in one piece (monolithically) with the at least one sealing element. This permits a particularly resilient formation of the at least one sealing element. The seal may rest on and/or enclose the further component so as to also provide protection against leaking liquids. A further advantage is that undesirably large gaps and/or joints between the components are avoided, that might otherwise be present due to conventional sealing elements, which are separately formed from the components, becoming detached. It is advantageously to dispense with an additional component for sealing, such as foam rubber beading, which is often used. There is also no projecting sealing lip, which might chafe the patient's skin.

In another embodiment of the invention, the at least one self-supporting cladding has a layer with a flame-retardant coating, on a side of the at least one self-supporting cladding that faces the detector. A flame-retardant coating herein means a coating that swells on contact with a flame and in this manner forms a flame barrier. The flame-retardant coating preferably is a resilient flame-retardant coating, such that, in the event of resilient deformation of the self-supporting cladding, a continuous coating layer is retained and cracking of the coating layer can be prevented. This additionally permits a high standard of safety for the housing of the medical imaging apparatus. By using the flame-retardant coating, the resilience of the resilient cladding layer is not impaired, since, for example, resilient foams with a high flame retardant content lose their resilient properties to a large extent.

The at least one self-supporting cladding may have at least one further flame-retardant element, arranged on the side of the at least one self-supporting cladding that faces the detector. For example, the further flame-retardant element may be a flame-retardant nonwoven material, which may be arranged on particularly critical and/or hazardous zones of the self-supporting cladding, such as on zones of the self-supporting cladding that rest against the housing and/or basic field magnet. A high standard of safety for the housing of the medical imaging apparatus is thereby achieved. Additional suppression and/or sealing with regard to the propagation of sound waves can be achieved by the additional flame-retardant element, in particular the flame-retardant nonwoven material. A further advantage is that the further flame-retardant element additionally performs a sealing function between the cladding and components surrounded by the cladding, such as the radio-frequency antenna of a magnetic resonance scanner. The further flame-retardant element preferably provides a sealing function in addition to that of a sealing element arranged on the cladding.

By using the flame-retardant coating together with the further flame-retardant element, particularly cost-effective flame retardancy is achieved.

In another embodiment, the at least one self-supporting cladding has at least one latching element on a side of the at least one self-supporting cladding that faces the detector. This permits simple and time-saving fastening of the self-supporting cladding to the housing and/or the medical imaging apparatus. Such visible fastening elements may be avoided on a side of the cladding remote from the detector. The latching element of the self-supporting cladding is preferably formed to correspond to (mate with) a further latching element of the housing and/or the medical imaging apparatus. The latching element may here be formed separately from the cladding, with the latching element being arranged on the cladding, in particular on the reinforcing grid thereof. To this end, the reinforcing grid preferably has a receiving element, such as a cylinder-like extension or a foamed-in-place threaded bushing or a projection, on which the latching element is arranged.

In another embodiment of the invention, the at least one self-supporting cladding has at least one recess with a recessed grip on a side of the at least one cladding remote from the detector. This permits simple and time-saving fastening of the at least one self-supporting cladding to the housing and/or to the medical imaging apparatus. In this manner, a latching connection between the latching elements can be simply and rapidly unlatched or detached by pulling on the recessed grip, due to the resilient nature of the cladding, with the user standing on a side remote from the detector, and the latching element in contrast being on a side of the at least one self-supporting cladding that faces the detector. This also permits simple disassembly of the self-supporting cladding, as is required during maintenance and/or servicing of the medical imaging apparatus.

In another embodiment of the invention, the at least one self-supporting cladding has at least one ventilation duct with an enclosure, the enclosure being formed as two half-shells. At least one of the two half-shells of the enclosure of the at least one ventilation duct is preferably integrated within the reinforcing grid of the self-supporting cladding. The two half-shells of the enclosure of the at least one ventilation duct are produced from a material and by a production method identical to those of the reinforcing grid.

As a result, rounded portions of the at least one ventilation duct are obtained that have no undesirable corners or edges. Undesirable turbulence of a stream of air guided through the ventilation duct is thus avoided. A further advantage is that the shape and/or course of the ventilation duct is established right from the production of the reinforcing grid, resulting in the provision of an advantageous outlet orifice with a angle of $30°\pm15°$ in the patient accommodation zone.

A subzone of the resilient cladding layer is preferably arranged between the two half-shells of the at least one ventilation duct. The two half-shells of the at least one ventilation duct are preferably firmly connected together. For example, the two half-shells of the enclosure of the at least one ventilation duct are screwed together. By arranging a subzone of the resilient cladding layer between the two half-shells, sealing of the at least one ventilation duct is achieved. The subzone of the resilient cladding layer is preferably limited to zones, of the two half-shells of the at least one ventilation duct that rest on one another.

In another embodiment of the invention, the two half-shells of the at least one ventilation duct are formed by the reinforcing grid. An advantageous stability of the at least one ventilation duct is thereby achieved. The two half-shells of the at least one ventilation duct are preferably integrated within the reinforcing grid and produced from the same material as the reinforcing grid. This embodiment of the invention has the additional advantage of making it possible to dispense with adhesives and/or sealants during the production and/or installation of the at least one ventilation duct. In addition, the ventilation duct may have ventilation nozzles, which may be arranged by fastening clips, at an air outlet orifice of the duct.

The at least one self-supporting cladding can have at least one support element, such as at least one support foot on which the self-supporting cladding can be placed when disassembled from the medical imaging apparatus. Peripheral zones of the self-supporting cladding, such as sealing elements etc., are thus advantageously protected from undesirable damage and/or deformation.

The at least one self-supporting cladding can be formed to be, or have, a cladding funnel. Such a cladding funnel is arranged on the front side or the rear side of the detector, around each or one end region of the patient accommodation zone (patient tunnel or bore). This has the advantage of making the cladding compact, particularly in noise-emitting and/or noise-transmitting zones of a medical imaging apparatus, such as a magnetic resonance apparatus. Such a cladding additionally permits advantageous noise suppression during operation of the medical imaging apparatus, such as a magnetic resonance apparatus. Using the least one self-supporting cladding as a cladding funnel on the front side or rear side of the detector additionally permits a visually smooth transition from the front side or rear side to the patient accommodation zone cladding of the housing.

DESCRIPTION OF THE PREFERRED EMBODIMENTS

Figure 1:
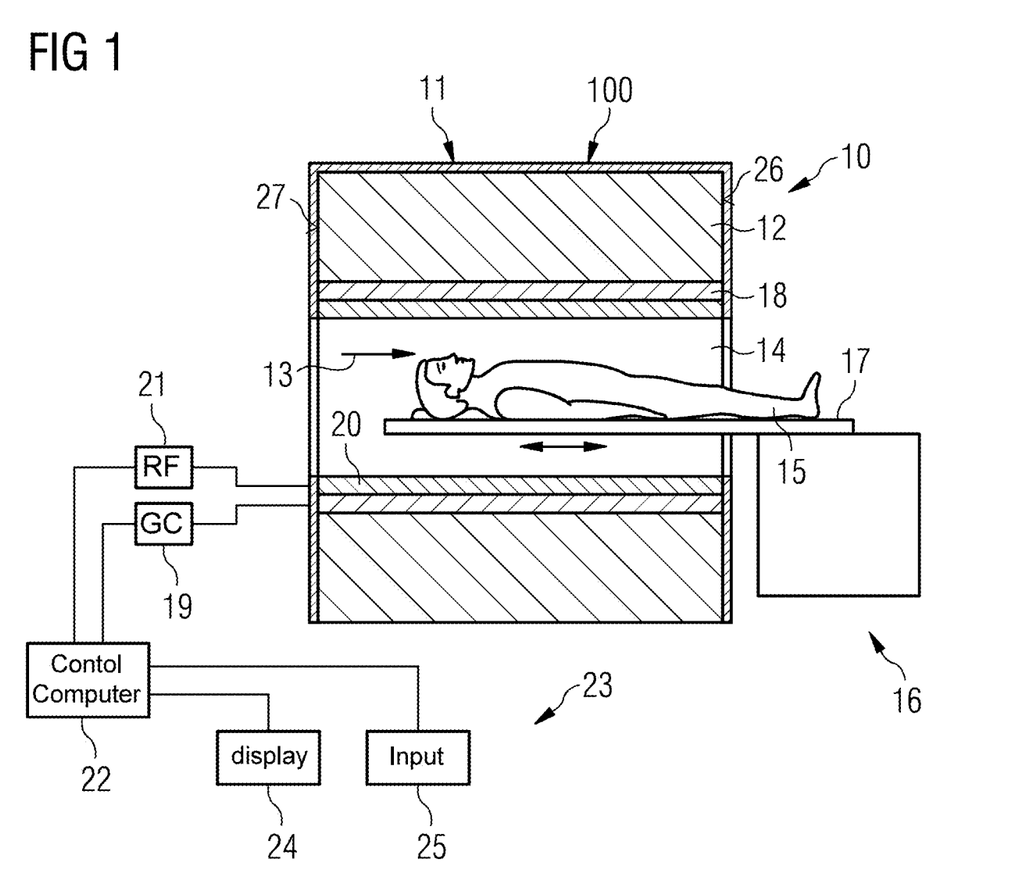
FIG. 1 schematically illustrates a medical imaging apparatus.

FIG. 1 schematically shows a medical imaging apparatus. In the present exemplary embodiment, the medical imaging apparatus is a magnetic resonance apparatus 10, so the present invention is explained using the example of the magnetic resonance apparatus 10. The present invention, however, is not limited to a configuration as a magnetic resonance apparatus 10, and further configurations of the medical imaging apparatus are possible.

The magnetic resonance apparatus 10 has a detector formed by a scanner 11. The scanner 11 has a superconducting basic field magnet 12 that generates a strong and constant basic magnetic field 13. The magnetic scanner 11 has a patient accommodation zone 14 for accommodating a patient 15. In the present exemplary embodiment, the patient accommodation zone 14 is of cylindrical shape and is circumferentially surrounded by the scanner 11. In principle, however, the patient accommodation zone 14 may formed in a manner that differs therefrom. The patient 15 can be advanced into the patient accommodation zone 14 by a patient positioning apparatus 16. The patient positioning apparatus 16 has a patient table 17 that is movable within the patient accommodation zone 14.

The scanner 11 furthermore has a gradient coil arrangement 18 that generates magnetic field gradients, which are used for spatially encoding MR signals during imaging. The gradient coil arrangement 18 is controlled by a gradient controller 19. The scanner 11 furthermore has a radio-frequency antenna 20 controlled by a radio-frequency controller 21 so as to emit radio-frequency (RF) sequences into an examination volume that is substantially formed by the patient accommodation zone 14. The radiated RF sequence gives certain nuclear spins in the patient 15 a magnetization that causes those excited nuclear spins to deviate from the basic magnetic field 13, by an amount known as a flip angle. As those excited nuclear spins relax and return to the study state, they emit the aforementioned MR signals, which are also RF signals. Those MR signals are detected by the same antenna from which the RF sequence was emitted, or by a different antenna.

The magnetic resonance apparatus 10 has a system control computer 22 that controls the basic field magnet 11 and the gradient controller 19 and the radio-frequency controller 21. The system control computer 22 provides central control of the magnetic resonance apparatus 10, such as the performance of a predetermined imaging gradient echo sequence. In addition, the system control computer 22 has an evaluation processor (not shown) for evaluating medical image data acquired during the magnetic resonance examination. The magnetic resonance apparatus 10 furthermore has a user interface 23 connected to the system control computer 22. Control information, such as imaging parameters, and reconstructed magnetic resonance images, can be displayed on a display unit 24, for example on at least one monitor, which presents the user interface 23 to a medical operator. The user interface 23 furthermore has an input unit 25, via which information and/or parameters may be entered by the medical operator during a measurement procedure.

Figure 2:
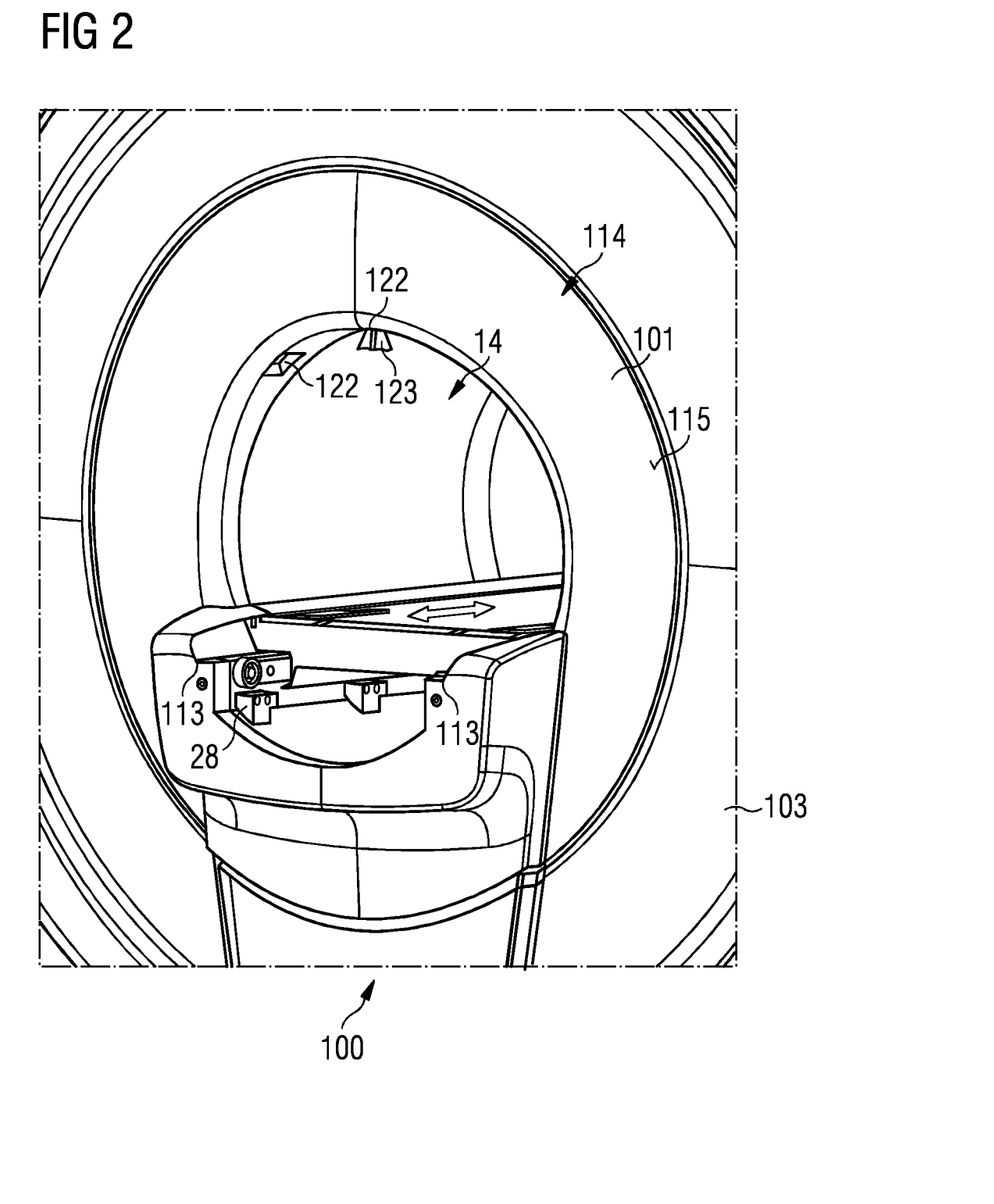
FIG. 2 schematically illustrates a cladding according to the invention, arranged on a rear side of the medical imaging apparatus.
Figure 3:
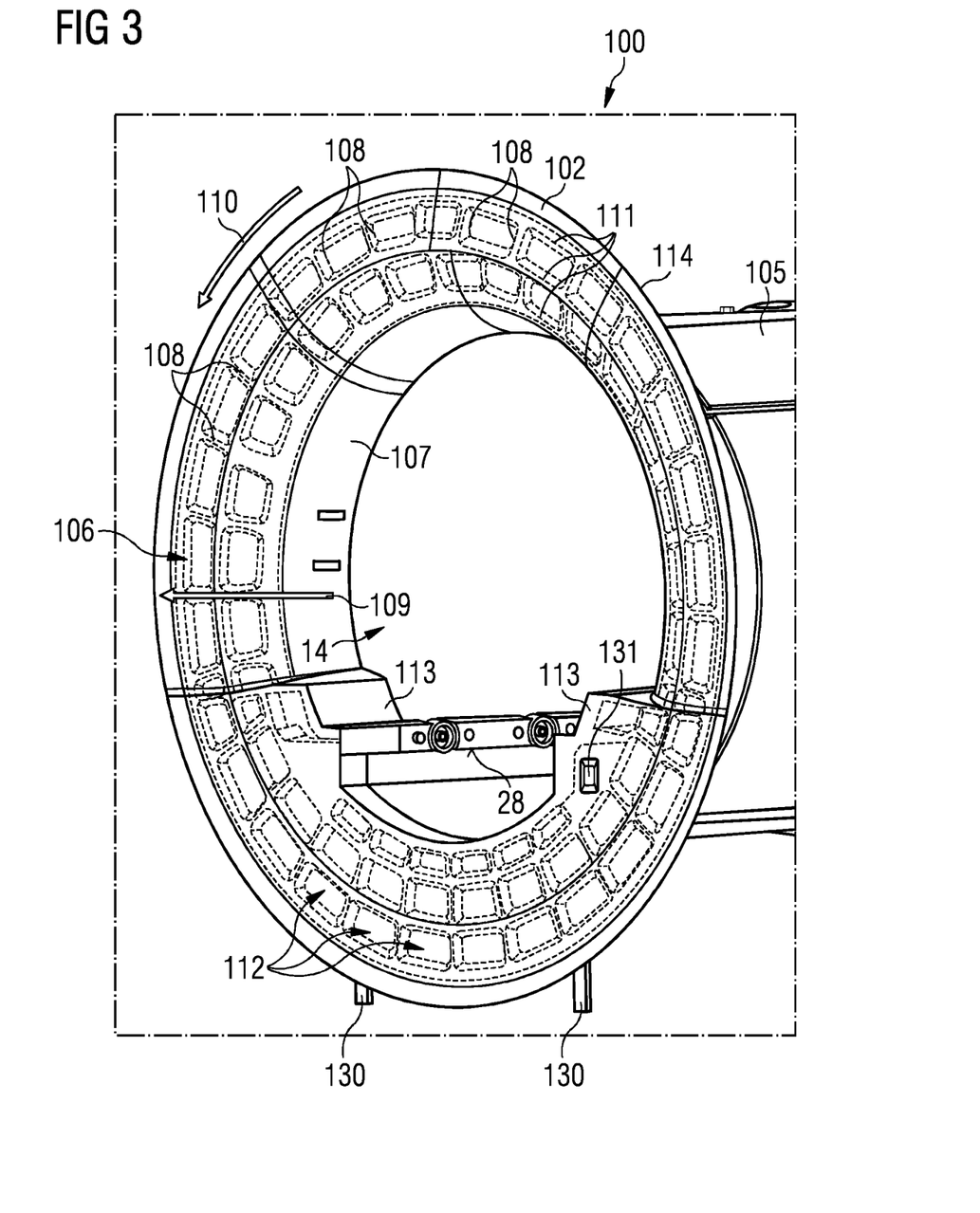
FIG. 3 schematically illustrates a cladding according to the invention, arranged on a front side of the medical imaging apparatus.

The magnetic resonance apparatus 10 furthermore has a housing 100 that surrounds the scanner 11. The housing 100 has a first cladding that is a first self-supporting cladding 101 (FIG. 2). In addition, the housing 100 has a second cladding that is a second self-supporting cladding 102 (FIG. 3). The first cladding 101 and the second cladding 102 are in each case formed as a cladding funnel and are respectively arranged at the end zones of the patient accommodation zone 14 of the scanner 11 The cladding funnels in each case surround a transitional zone from the patient accommodation zone 14 to a front side 26 or a rear side 27 of the scanner 11. The cladding funnels in each case cover the transitional zone from the patient accommodation zone 14 to the front side 26 or to the rear side 27 of the scanner 11.

The housing 100 has further claddings 103, 104, 105. the further cladding 103 here is a front cladding, which is arranged as an annular disk on the front side 26 of the scanner 11. The front cladding 103, together with the front side 26 cladding funnel, covers the front side 26 of the scanner 11. A further cladding 104 is a rear cladding, which is arranged as an annular disk on the rear side 27 of the scanner 11. The rear cladding 104, together with the rear side 27 cladding funnel, covers the rear side 27 of the scanner 11. A further cladding 105 is a patient accommodation zone cladding, which cylindrically surrounds the patient accommodation zone 14. The front side 26 cladding funnel is arranged between the patient accommodation zone cladding 105 and the front cladding 103. The rear side 27 cladding funnel is arranged between the patient accommodation zone cladding 105 and the rear cladding 104.

The two self-supporting claddings 101, 102, in particular the two cladding funnels, are shown in greater detail in FIGS. 2 to 6. The two self-supporting claddings 101, 102, in particular the two cladding funnels, each have a reinforcing grid 106 and a resilient cladding layer 107. The configurations and characteristics of the two self-supporting claddings 101, 102 are explained below for the individual self-supporting cladding 102, and the other of the two self-supporting claddings 101 also has the same characteristics and configurations.

FIG. 3 shows the self-supporting cladding 102 in the example of a cladding funnel arranged on the front side 26 of the scanner 11. The reinforcing grid 106 of the self-supporting cladding 102 is surrounded by the resilient cladding layer 107, and is thus not visible from the outside, and therefore is shown only in dashed lines. The reinforcing grid 106 is of funnel-shaped construction and is a uniform reinforcing grid. The uniform reinforcing grid 106 has grid rods 108 extending in the radial direction 109, with the spacings in the circumferential direction 110 of the reinforcing grid 106 between each two adjacent grid rods 108 are equal. The reinforcing grid 106 has further grid rods 111 that are arranged concentrically to one another. The concentric grid rods 111 connect together the grid rods 108 that extend in the radial direction 109. In the present exemplary embodiment, the reinforcing grid 106 has three concentric grid rods 111. The concentric grid rods 111 are annular in form (FIG. 3).

Two adjacent grid rods 108 extending in the radial direction 109 and two adjacent, concentrically arranged grid rods 111 thus each enclose a grid interspace 112 in planar manner. The individual grid interspaces 112 are here trapezoidal in shape. The individual grid rods 108, 111 of the reinforcing grid 106 have a spacing of at least 1 cm or a spacing of at least 2 cm or a spacing of at least 3 cm. The individual grid rods 108, 111 furthermore have a spacing of at most 30 cm or a spacing of at most 25 cm or a spacing of at most 20 cm or a spacing of at most 15 cm. The individual grid rods 108, 111 preferably have a spacing of at least 4 cm and at most 6 cm. The reinforcing grid 106 has a thickness of approx. 12 mm.

In a zone of a guide 28 of the patient table 17, the reinforcing grid 106 has additional reinforcing elements 113. The additional reinforcing elements 113 of the reinforcing grid 106 are arranged on each side of the reinforcing grid 106 in an introduction zone of the patient table 17. The two reinforcing elements 113 each have a stepped construction. An advantageous seal between the self-supporting claddings 101, 102 and the patient table 17 is thus obtained. This also increases patient safety, since trapping and/or crushing of body parts between the self-supporting claddings 101, 102 and the patient table 17 is prevented.

The reinforcing grid 106 is formed of a material that has a Shore D hardness of at least 60 and at most 70 or a Shore D hardness of at least 61 and at most 69 or a Shore D hardness of at least 62 and at most 68 or a Shore D hardness of at least 63 and at most 67 or a Shore D hardness of at least 64 and at most 66. The reinforcing grid 106 preferably is formed of a material with a Shore D hardness of 65. The material of the reinforcing grid 106 preferably is an elastomer, in particular a tough elastomer, such as a rigid foam or a rigid structural foam.

The reinforcing grid 106 is arranged at least partially embedded within the resilient cladding layer 107. The grid rods 108, 111 are here preferably surrounded on all sides by the resilient cladding layer 107. The grid interspaces 112 of the reinforcing grid 106 are additionally at least partially filled with the resilient cladding layer 107. In particular, the grid interspaces 112 of the reinforcing grid 106 are completely filled with the resilient cladding layer 107 (FIG. 3). The self-supporting claddings 101, 102 each have a thickness, in particular a material thickness, of approx. 20 mm.

The resilient cladding layer 107 is formed of a material that has a Shore A hardness of at least 50 and at most 70 or a material with a Shore A hardness of at least 52 and at most 68 or a material with a Shore A hardness of at least 54 and at most 66 or a material with a Shore A hardness of at least 56 and at most 64 or a material with a Shore A hardness of at least 58 and at most 62. The resilient cladding layer 107 preferably is formed of a material with a Shore A hardness of 60. The material of the resilient cladding layer 107 preferably is an elastomer, in particular a flexible elastomer, such as a foam or a flexible structural foam.

Figure 4:
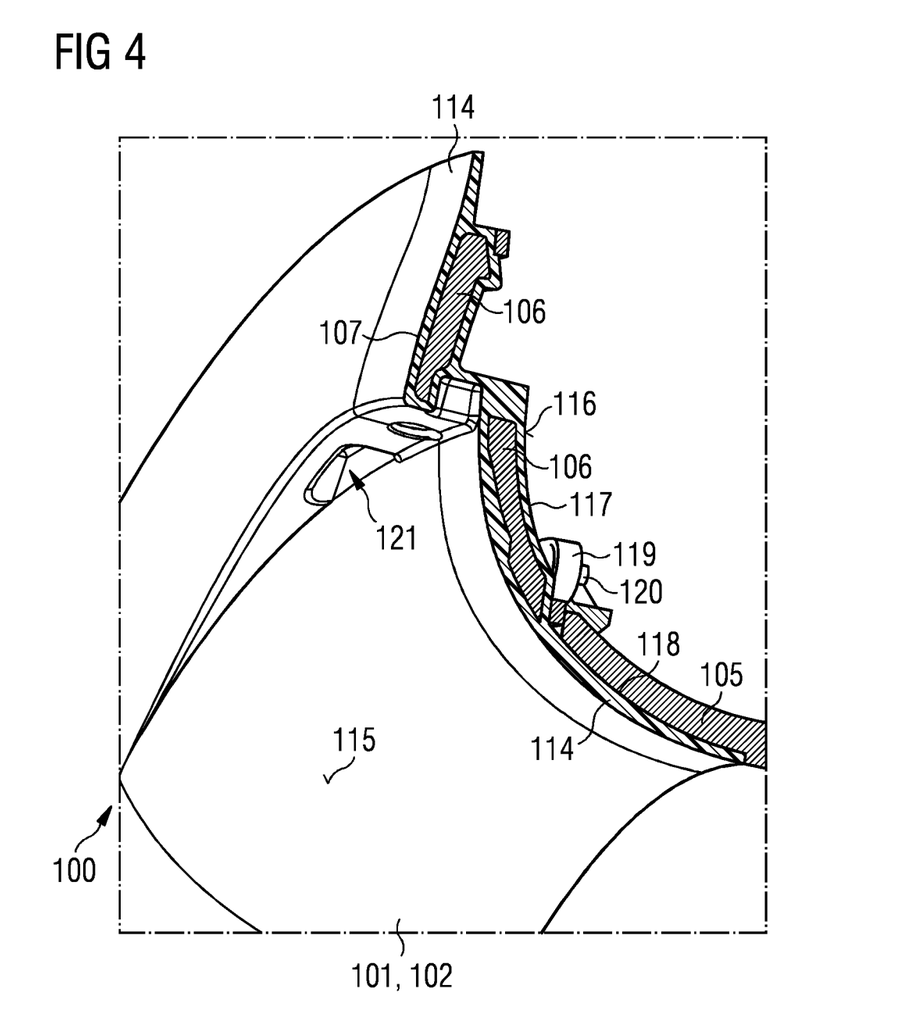
FIG. 4 schematically illustrates a first view of a section through the cladding.
Figure 5:
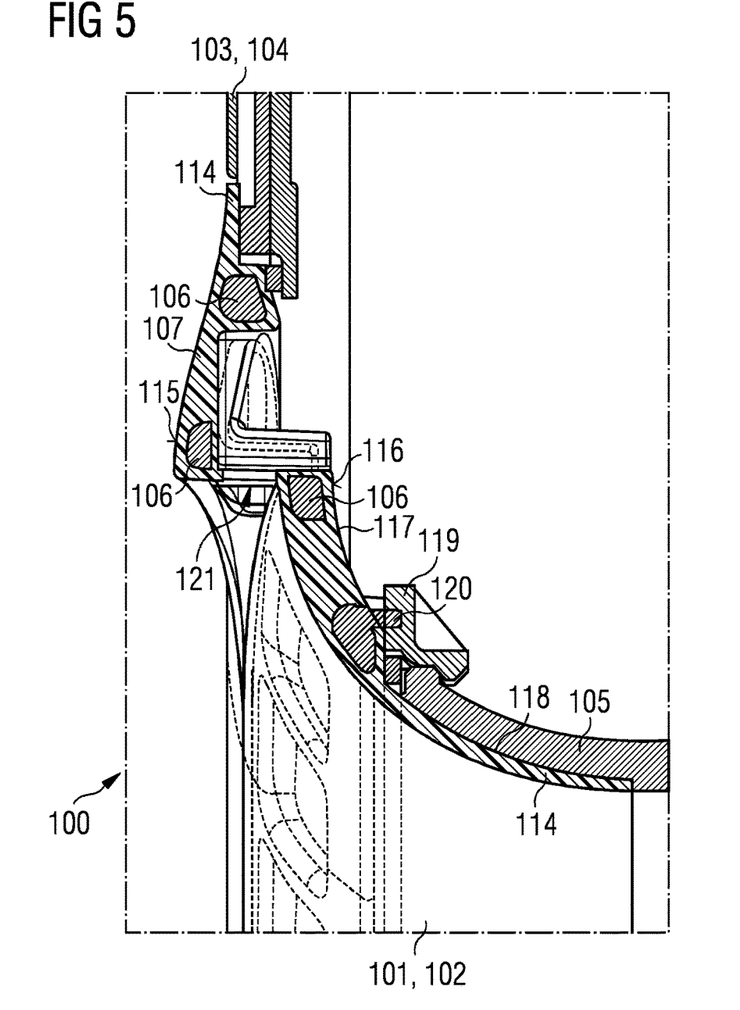
FIG. 5 schematically illustrates a second view of a section through the cladding.

At the peripheral zones of the self-supporting claddings 101, 102, with which the self-supporting claddings 101, 102 adjoin a further cladding 103, 104, 105, in particular the patient accommodation zone cladding and/or the front cladding and/or the rear cladding, the self-supporting claddings 101, 102 each have a sealing element 114. The sealing elements 114 are formed by the resilient cladding layer 107. The sealing elements 114 can be formed in one piece with the resilient cladding layer 107. In these peripheral zones, thus in zones in which sealing elements 114 are arranged, the self-supporting claddings 101, 102 preferably have a thickness of approx. 4 mm (FIGS. 4 and 5).

The self-supporting claddings 101, 102 has a side 115 remote from the detector, in particular the scanner 11. The resilient cladding layer 107 has a surface of the side 115 remote from the detector (FIGS. 2, 4 and 5). The self-supporting claddings 101, 102 furthermore have a side 116 which faces the detector, in particular the scanner 11. On a surface of the side of the self-supporting cladding 101, 102 which faces the detector, in particular the scanner 11, the self-supporting cladding 101, 102 has a layer with a flame-retardant coating 117. The flame-retardant coating 117 preferably is a resilient flame-retardant coating 117, such that the resilience of the resilient cladding layer 107 is not restricted (FIGS. 4 and 5).

The self-supporting cladding 101, 102 furthermore has a further flame-retardant element 118, which is likewise arranged on the side 116 of the self-supporting cladding 101, 102 that faces the scanner 11. In the exemplary embodiment, the further flame-retardant element 118 is a flame-retardant nonwoven material (FIGS. 4 and 5).

The self-supporting cladding 101, 102 additionally has a number of latching elements 119 for fastening the self-supporting cladding 101, 102 to the housing 100 and/or the scanner 11. FIGS. 4 and 5 each show just one latching element 119. The latching elements 119 are arranged on the side 116 of the self-supporting cladding 101, 102 that faces the detector. To this end, the self-supporting cladding 101, 102 has receiving elements 120 on the side 116 that faces the detector, and on which the latching elements 119 are arranged. In the exemplary embodiment, the receiving elements 120 are of cylindrical construction. The receiving elements 120 are additionally formed by the reinforcing grid 106 and are formed in one piece therewith.

For assembly and/or disassembly of the self-supporting claddings 101, 102, the self-supporting claddings 101, 102 have recesses 121 on a side 115 remote from the detector. These recesses 121 each have a recessed grip that can be gripped by a user. Simple assembly and/or disassembly is enabled by the recesses 121, in particular the recessed grips. For example, by pulling on the recessed grip, and due to the resilient nature of the self-supporting cladding 101, 102, the latching connections between the self-supporting claddings 101, 102 and the scanner 11 may be undone and/or unlatched.

In addition, the self-supporting cladding funnel 102 has two holding elements 130 (FIG. 3). The two supporting elements 130 are designed to support the self-supporting cladding funnel 101, 102 when in a disassembled state. The two supporting elements 130 are in the form of supporting feet.

The previous explanations relate both to a self-supporting cladding 102 in the form of a cladding funnel, which is arranged between the patient accommodation zone cladding and the front cladding and to a self-supporting cladding 101 in the form of a cladding funnel which is arranged between the patient accommodation zone cladding and the rear cladding.

The following explanations, however, relate to configurations which only apply to the self-supporting cladding 101 in the form of a cladding funnel, which is arranged between the patient accommodation zone cladding and the rear cladding. The self-supporting cladding 101, which is arranged between the patient accommodation zone cladding and the rear cladding additionally has recesses 122, which are provided for the arrangement of lighting elements and/or adjusting elements 123, such as for example an adjusting laser (FIG. 2). The recesses 122 for the arrangement of lighting elements and/or the adjusting laser are here arranged on the side of the self-supporting cladding 101 opposite the patient table 17.

The following explanations relate to configurations that only apply to the self-supporting cladding 102 in the form of a cladding funnel arranged between the patient accommodation zone cladding and the front cladding. The self-supporting cladding 102 additionally has a reflector 131.

Figure 6:
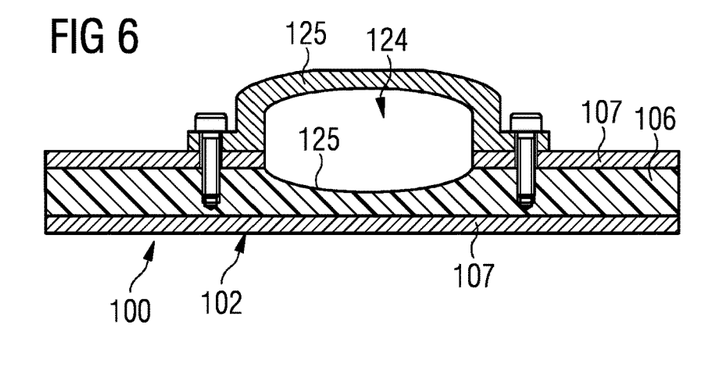
FIG. 6 schematically illustrates a section through the cladding with a ventilation duct.

The self-supporting cladding 102 that is between the patient accommodation zone cladding and the front cladding additionally has at least one ventilation duct 124 (FIG. 6).

The ventilation duct 124 has an enclosure formed by two half-shells 125. A first of the two half-shells 125 is formed by the reinforcing grid 106 and is formed in one piece therewith. A second of the two half-shells 125 is formed of a material identical to that of the reinforcing grid 106. The two half-shells 125 are screwed together. A subzone of the resilient cladding layer 107 is arranged between the two half-shells 125 for sealing the ventilation duct 124. The subzones of the resilient cladding layer 107 are arranged between zones of the two half-shells 125 that rest on one another. The two half-shells 125 form a ventilation duct 124 with a substantially oval cross-sectional area. The ventilation duct 124 may have additional ventilation nozzles, which may be arranged by fastening clips, at an air outlet orifice.

The present invention has been explained and depicted on the basis of two self-supporting claddings 101, 102. The present invention is, however, not limited to a housing 100 with precisely two self-supporting claddings 101, 102. In an alternative configuration of the invention, the housing 100 may have just one self-supporting cladding 101 or 102, or more than two self-supporting claddings 101, 102.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A medical imaging apparatus comprising:
   a medical image data detector; and
   a housing that at least partially surrounds said detector, said housing including at least one self-supporting cladding having a reinforcing grid with a resilient cladding layer, wherein said reinforcing grid includes grid interspaces that are at least partially filled with said resilient cladding layer.

2. A medical imaging apparatus as claimed in claim 1 wherein said reinforcing grid is at least partially embedded within said resilient cladding layer.

3. A medical imaging apparatus as claimed in claim 1 wherein said reinforcing grid is a uniform reinforcing grid.

4. A medical imaging apparatus as claimed in claim 1 wherein said reinforcing grid comprises at least two grid rods situated concentrically relative to each other.

5. A medical imaging apparatus as claimed in claim 1 wherein said reinforcing grid comprises at least two grid rods that planarly enclose a grid interspace, said at least two grid rods being arranged trapezoidally around said grid interspace.

6. A medical imaging apparatus as claimed in claim 5 wherein said at least two grid rods have a spacing therebetween of at least 3 cm and at most 30 cm.

7. A medical imaging apparatus as claimed in claim 1 wherein said reinforcing grid is comprised of a material having a Shore D hardness of at least 50 and at most 70.

8. A medical imaging apparatus as claimed in claim 1 wherein said reinforcing grid is comprised of a material having a Shore A hardness of at least 50 and at most 70.

9. A medical imaging apparatus as claimed in claim 1 wherein said self-supporting cladding has a side remote from said detector, and wherein said resilient cladding layer has a surface at said side remote from said detector.

10. A medical imaging apparatus as claimed in claim 1 wherein said housing comprises a further cladding and wherein said at least one self-supporting cladding comprises at least one sealing element on a peripheral zone of said at least one self-supporting cladding, said peripheral zone adjoining said further cladding.

11. A medical imaging apparatus as claimed in claim 10 wherein said at least one sealing element of said at least one self-supporting cladding is comprised in said resilient cladding layer of said at least one self-supporting cladding.

12. A medical imaging apparatus as claimed in claim 1 wherein said at least one self-supporting cladding comprises a layer with a flame-retardant coating, said layer with said flame-retardant coating being situated on a side of said at least one self-supporting cladding that faces said detector.

13. A medical imaging apparatus as claimed in claim 12 wherein said at least one self-supporting cladding comprises at least one further flame-retarding element, situated on said side of said at least one self-supporting cladding that faces said detector.

14. A medical imaging apparatus as claimed in claim 1 wherein said at least one self-supporting cladding comprises at least one latching element on a side of said at least one self-supporting cladding unit that faces said detector.

15. A medical imaging apparatus as claimed in claim 14 wherein said at least one self-supporting cladding comprises at least one recess with a recessed grip at a side of said at least one self-supporting cladding remote from said detector.

16. A medical imaging apparatus as claimed in claim 1 wherein said at least one self-supporting cladding comprises at least one ventilation duct having an enclosure formed by two joined half-shells.

17. A medical imaging apparatus as claimed in claim 16 comprising a sub-zone of said resilient cladding layer situated between said two half-shells of said at least one ventilation duct.

18. A medical imaging apparatus as claimed in claim 16 wherein at least one of said two half-shells of said at least one ventilation duct is formed by said reinforcing grid.

19. A medical imaging apparatus as claimed in claim 1 wherein said at least one self-supporting cladding comprises at least one exterior support element on which said at least one self-supporting cladding can rest when said at least one self-supporting cladding is removed from said detector.

20. A medical imaging apparatus as claimed in claim 1 wherein said detector has a patient accommodation zone that proceeds through said detector having opposite end regions, and wherein said at least one self-supporting cladding comprises a cladding funnel situated at either a front side or a rear side of said detector, around one of said end regions of said patient accommodation zone.

21. A medical imaging apparatus comprising:
   a medical image data detector; and
   a housing that at least partially surrounds said detector, said housing including at least one self-supporting cladding having a reinforcing grid with a resilient cladding layer,
   wherein said at least one self-supporting cladding includes at least one ventilation duct having an enclosure formed by two joined half-shells, at least one of said two half-shells of said at least one ventilation duct being formed by said reinforcing grid.

* * * * *